US006078838A

United States Patent [19]

Rubinstein

[11] Patent Number: 6,078,838

[45] Date of Patent: Jun. 20, 2000

[54] PSEUDOSPONTANEOUS NEURAL STIMULATION SYSTEM AND METHOD

[75] Inventor: Jay Rubinstein, Solon, Iowa

[73] Assignee: University of Iowa Research Foundation, Iowa City, Iowa

[21] Appl. No.: 09/023,278

[22] Filed: Feb. 13, 1998

[51] Int. Cl.[7] .......... A61N 1/36

[52] U.S. Cl. .......... 607/55

[58] Field of Search .......... 607/55–57, 137; 623/10; 600/25

[56] References Cited

U.S. PATENT DOCUMENTS

| | | | |
|---|---|---|---|
| 3,543,246 | 11/1970 | Puharich et al. | 607/55 |
| 3,881,495 | 5/1975 | Pannozzo et al. | 607/55 |
| 4,510,936 | 4/1985 | Fourcin et al. | 128/419 |
| 4,515,158 | 5/1985 | Patrick et al. | 128/419 |
| 4,577,641 | 3/1986 | Hochmair et al. | 128/746 |
| 4,593,696 | 6/1986 | Hochmair et al. | 128/419 |
| 4,611,596 | 9/1986 | Wasserman | 128/419 |
| 4,648,403 | 3/1987 | Van Compernolle | 128/419 |
| 5,061,282 | 10/1991 | Jacobs | 623/10 |
| 5,095,904 | 3/1992 | Seligman et al. | 128/420.6 |
| 5,215,085 | 6/1993 | von Wallenberg-Pachaly | 128/420.6 |
| 5,271,397 | 12/1993 | Seligman et al. | 607/137 |
| 5,549,658 | 8/1996 | Shannon et al. | 607/57 |
| 5,597,380 | 1/1997 | McDermott et al. | 607/57 |
| 5,601,617 | 2/1997 | Loeb et al. | 607/56 |
| 5,649,970 | 7/1997 | Loeb et al. | 607/57 |
| 5,735,885 | 4/1998 | Howard, III et al. | 607/55 |

FOREIGN PATENT DOCUMENTS 2 171 605 9/1986 United Kingdom .

OTHER PUBLICATIONS

Ifukube et al., "Design Of An Implantable Tinnitus Suppressor By Electrical Cochlear Stimulation", Biomechanics, Rehabilitation, Electrical Phenomena, Biomaterials, San Diego, Oct. 28–31, 1993, vol. 3, No. Conf. 15, pp. 1349–1350.

Cohen, N.L. et al., "A Prospective, Randomized Study of Cochlear Implants," *N. Engl. J. Med.*, 328:233–7, 1993.

*Primary Examiner*—Jeffrey R. Jastrzab
*Attorney, Agent, or Firm*—Fleshner & Kim

[57] ABSTRACT

A signal processing apparatus and method for neural stimulation is provided that can generate stochastic independent activity across an excited nerve or neural population. High rate pulse trains, for example, can produce random spike patterns in auditory nerve fibers that are statistically similar to those produced by spontaneous activity in the normal ear. This activity is called "pseudospontaneous activity". Varying rates of pseudospontaneous activity can be created by varying the intensity of a fixed amplitude, high rate pulse train stimulus, e.g., 5000 pps. The pseudospontaneous activity can eliminate a major difference between acoustic- and electrical-derived hearing percepts. The pseudospontaneous activity can further desynchronize the nerve fiber population as a treatment for tinnitus.

23 Claims, 12 Drawing Sheets

PSEUDOSPONTANEOUS NEURAL STIMULATION SYSTEM AND METHOD

Part of the work performed during the development of this invention utilized U.S. Government funds under grant DC 62111 and contract OD 02948 from the National Institute of Health. The government may have certain rights in this invention.

BACKGROUND OF THE INVENTION

1. Field of the Invention

This invention relates generally to an apparatus and method for providing stochastic independent neural stimulation, and in particular, a neural stimulation system and method for providing pseudospontaneous activity in the auditory nerve, which can be used to treat tinnitus.

2. Related Applications

Co-pending patent application U.S. Ser. No. 09/023,279, entitled "Speech Processing System and Method Using Pseudospontaneous Stimulation", by J. Rubinstein and B. Wilson (Attorney Docket No. UIOWA-26) filed Feb. 13, 1998, containing related subject matter, is hereby incorporated by reference.

3. Background of the Related Art

Fundamental differences currently exist between electrical stimulation and acoustic stimulation of the auditory nerve. Electrical stimulation of the auditory nerve, for example, via a cochlear implant, generally results in more cross-fiber synchrony, less within fiber jitter, and less dynamic range, as compared with acoustic stimulation which occurs in individuals having normal hearing. FIG. 14 shows the magnitude of a related art pattern of electrically-evoked compound action potentials (EAPs) from an auditory nerve of a human subject with an electrical stimulus of 1 kHz (1016 pulses/s). The EAP magnitudes are normalized to the magnitude of the first EAP in the record. FIG. 14 shows the typical alternating pattern previously described in the art. This pattern arises because of the refractory period of the nerve and can degrade the neural representation of the stimulus envelope. With a first stimulus 1402 a large response occurs, likely because of synchronous activation of a large number of fibers. These fibers are subsequently refractory driving a second pulse 1404, and accordingly a small response is generated. By the time of a third pulse 1406, an increased pool of fibers becomes available (non-refractory) and the corresponding response increases. The alternating synchronized response pattern can be caused by a lack or decrease of spontaneous activity in the auditory nerve and can continue indefinitely. Variations of the alternative response pattern and more complex patterns have been observed in human (e.g., with different rates of amplitudes of stimulation), animal and modeling studies. Such complex patterns of response at the periphery may indicate limitations in the transmission of stimulus information to the central nervous system as they may reflect properties of the auditory nerve in addition to properties of the stimulus.

Loss of spontaneous activity in the auditory nerve is one proposed mechanism for tinnitus. Tinnitus is a disorder where a patient experiences a sound sensation within the head ("a ringing in the ears") in the absence of an external stimulus. This uncontrollable ringing can be extremely uncomfortable and often results in severe disability. Restoration of spontaneous activity may potentially improve tinnitus suppression. Tinnitus is a very common disorder affecting an estimated 15% of the U.S. population according to the National Institutes for Health, 1989 National Strategic Research Plan. Hence, approximately 9 million Americans have clinically significant tinnitus with 2 million of those being severely disabled by the disorder.

Several different types of treatments for tinnitus have been attempted. One related art approach to treating tinnitus involves suppression of abnormal neural activity within the auditory nervous system with various anticonvulsant medications. Examples of such anticonvulsant medications include xylocaine and lidocaine that are administered intravenously. In addition, since the clinical impact of tinnitus is significantly influenced by the patient's psychological state, antidepressants, sedatives, biofeedback and counseling methods are also used. None of these methods has been shown to be consistently effective.

Another related art approach to treating tinnitus involves "masking" undesirable sound perception by presenting alternative sounds to the patient using an external sound generator. In particular, an external sound generator is attached to the patient's ear (similar to a hearing aid) and the generator outputs sounds into the patient's ear. Although this approach has met with moderate success, it has several significant drawbacks. First, such an approach requires that the patient not be deaf in the ear that uses the external sound generator. That is, the external sound generator approach cannot effectively mask sounds to a deaf ear that subsequently developed tinnitus. Second, the external sound generator can be inconvenient to use and can actually result in loss of hearing acuity in an otherwise healthy ear.

Yet another related art approach involves surgical resection of the auditory nerve itself. This more dangerous approach is usually only attempted if the patient suffers from large acoustic neuromas as well as tinnitus. In this situation, the auditory nerve is not resected for the specific purpose of eliminating tinnitus but the auditory nerve can be removed as an almost inevitable complication of large tumor removal. In a wide series of patients with tinnitus who underwent this surgical procedure of auditory nerve resection, only 40% were improved, 10% were improved and 50% were actually worse.

SUMMARY OF THE INVENTION

An object of the present invention is to provide an apparatus and method of neural stimulation that substantially obviates at least some of the problems and disadvantages of the related art.

Another object of the present invention is to provide an apparatus and method that generates stochastically independent or pseudospontaneous neural activity.

Yet another object of the present invention is to provide an apparatus and method that generates pseudospontaneous activity in an auditory nerve to suppress tinnitus.

Still yet another object of the present invention is to provide an inner ear or middle ear auditory prosthesis that suppresses tinnitus.

A further object of the present invention is to provide an apparatus and method that uses electrical stimulation to increase or maximize stochastic independence of individual auditory nerve fibers to represent temporal detail in an auditory percept.

A still further object of the present invention is to provide an apparatus and method that delivers a prescribed signal such as a high rate pulse train to generate neural pseudospontaneous activity.

A still further object of the present invention is to provide an apparatus and method that increases hearing capability by providing a prescribed signal to auditory neurons.

To achieve at least the above objects in a whole or in parts, there is provided a method and apparatus according to the present invention for generating pseudospontaneous activity in a nerve that includes generating a electrical signal and applying the signal to the nerve to generate pseudospontaneous activity.

To further achieve at least the above objects in a whole or in parts, there is provided a neural prosthetic apparatus for treatment of a patient with tinnitus that includes a stimulation device that outputs one or more electrical signals that include transitions between first and second amplitudes occurring at a frequency greater than 2 kHz, an electrode arrangement along an auditory nerve of a patient having a plurality of electrical contacts arranged along the electrode, each of the plurality of electrical contacts independently outputting electrical discharges in accordance with the electrical signals and an electrical coupling device for electrically coupling the electrical contacts to the stimulation device, and wherein the neural prosthetic apparatus effectively alleviates the tinnitus of the patient.

To further achieve at least the above objects in a whole or in parts, there is provided a method for treating a patient with tinnitus according to the present invention that includes outputting one or more electrical signals, arranging a plurality of electrical contacts along a cochlea, wherein each of the plurality of electrical contacts independently outputs electrical discharges in accordance with the electrical signals and generating pseudospontaneous activity in an auditory nerve by electrically coupling the electrical contacts to the electrical signals, where the neural prosthetic apparatus effectively alleviates the tinnitus of the patients.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The auditory system is composed of many structural components, some of which are connected extensively by bundles of nerve fibers. The auditory system enables humans to extract usable information from sounds in the environment. By transducing acoustic signals into electrical signals, which are processed in the brain, humans can discriminate among a wide range of sounds with great precision.

Figure 1:
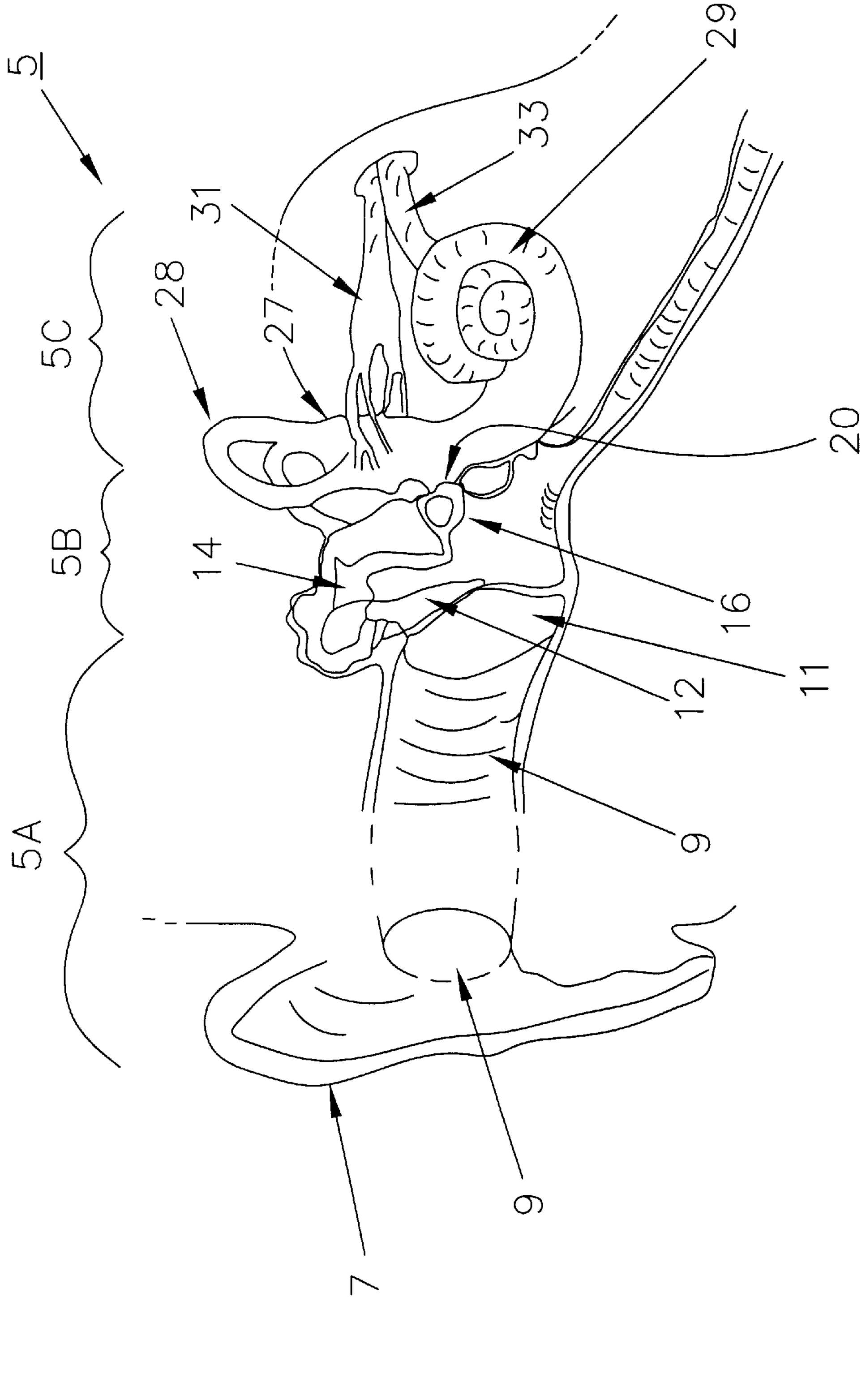
FIG. 1 is a diagram showing a section view of the human ear as seen from the front.

FIG. 1 shows a side cross-sectional view of a human ear 5, which includes the outer ear 5A, middle ear 5B and inner ear 5C. The outer ear 5A includes pinna 7 having folds of skin and cartilage and outer ear canal 9, which leads from the pinna 7 at its proximal end to the eardrum 11 at its distal end. The eardrum 11 includes a membrane extending across the distal end of the outer ear canal 9. The middle ear 5B is located between the eardrum 11 and the inner ear 5C and includes three small connected bones (ossicles), namely the hammer 12, the anvil 14, and the stirrup 16. The hammer 12 is connected to the inner portion of the eardrum 11, the stirrup 16 is attached to oval window 20, and the anvil 14 is located between and attached to each of the hammer 12 and the stirrup 16. A round or oval window 20 leads to the inner ear 5C. The inner ear 5C includes the labyrinth 27 and the cochlea 29, each of which is a fluid-filled chamber. The labyrinth 27, which is involved in balance, includes the semicircular canals 28. Vestibular nerve 31 attaches to the labyrinth 27. Cochlea 29 extends from the inner side of the round window 20 in a generally spiral configuration, and plays a key role in hearing by transducing vibrations transmitted from middle ear 5B into electrical signals for transmission along auditory nerve 33 to the hearing centers of the brain (FIGS. 2A and 2B).

In normal hearing, sound waves collected by the pinna 7 are funneled down the outer ear canal 9 and vibrate the eardrum 11. The vibration is passed to the ossicles (hammer 12, anvil 14, and stirrup 16). Vibrations pass through the round window 20 via the stirrup 16 causing the fluid within the cochlea 29 to vibrate. The cochlea 29 is equipped internally with a plurality of hair cells (not shown). Neurotransmitters released by the hair cells stimulate the auditory nerve 33 thereby initiating signal transmission along the auditory nerve 33. In normal hearing, the inner hair cell-spiral ganglion is inherently "noisy" in the absence of sound because of the random release of neurotransmitters from hair cells. Accordingly, in normal hearing, spontaneous activity in the auditory nerve occurs in the absence of sound.

Figure 2B:
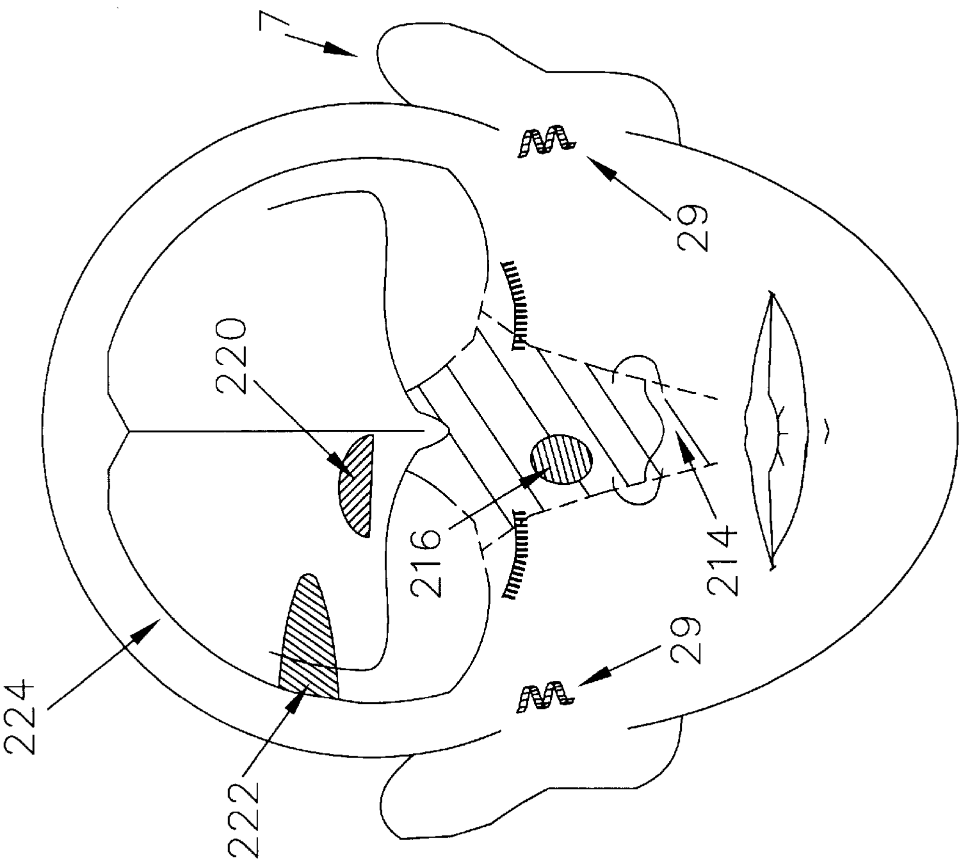
FIGS. 2A and 2B are diagrams showing the relative positions of the hearing elements including the external ear, auditory cortex, cochlea and cochlear nucleus.
Figure 2A:
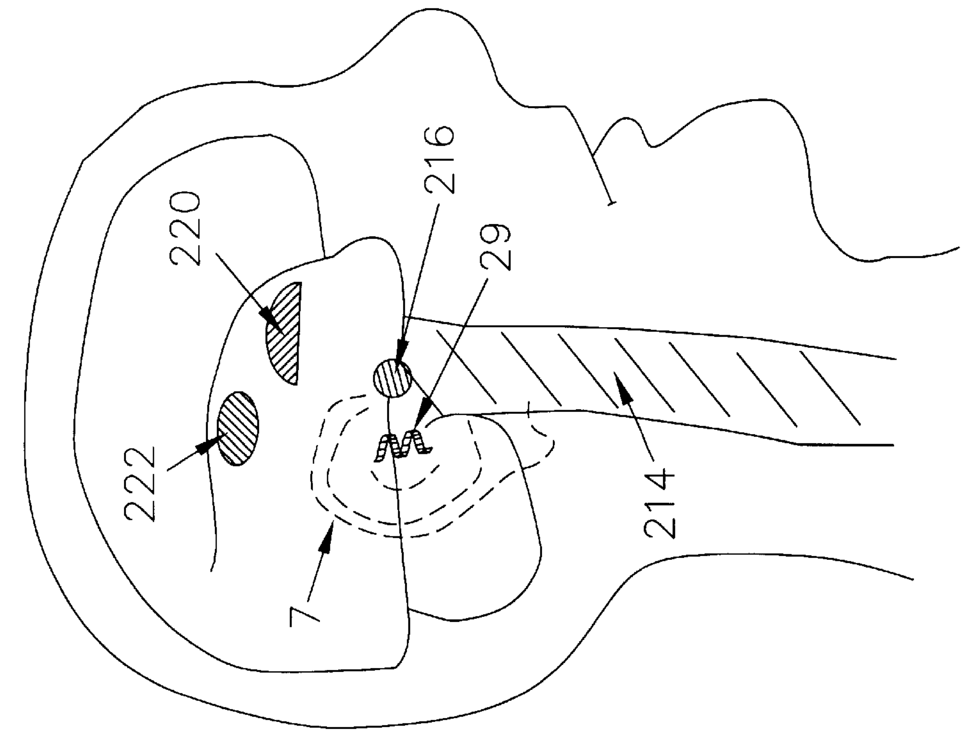

FIGS. 2A and 2B respectively show a side view and a front view of areas involved in the hearing process, including the pinna 7 and the cochlea 29. In particular, the normal transduction of sound waves into electrical signals occurs in the cochlea 29 that is located within the temporal bone (not shown). The cochlea 29 is tonotopically organized, meaning different parts of the cochlea 29 respond optimally to different tones; one end of the cochlea 29 responds best to high frequency tones, while the other end responds best to low frequency tones. The cochlea 29 converts the tones to electrical signals that are then received by the cochlea nucleus 216, which is an important auditory structure located in the brain stem 214. As the auditory nerve leaves the temporal bone and enters the skull cavity, it penetrates the brain stem 214 and relays coded signals to the cochlear nucleus 216, which is also tonotopically organized. Through many fiber-tract interconnections and relays (not shown), sound signals are analyzed at sites throughout the brain stem 214 and the thalamus 220. The final signal analysis site is the auditory cortex 222 situated in the temporal lobe 224.

Information is transmitted along neurons (nerve cells) via electrical signals. In particular, sensory neurons such as those of the auditory nerve carry information about sounds in the external environment to the central nervous system (brain). Essentially all cells maintain an electrical potential (i.e., the membrane potential) across their membranes. However, nerve cells use membrane potentials for the purpose of signal transmission between different parts of an organism. In nerve cells, which are at rest (i.e., not transmitting a nerve signal) the membrane potential is referred to as the resting potential (Vm). The electrical properties of the plasma membrane of nerve cells are subject to abrupt change in response to a stimulus (e.g., from an electrical impulse or the presence of neurotransmitter molecules), whereby the resting potential undergoes a transient change called an action potential. The action potential causes electrical signal transmission along the axon (i.e., conductive core) of a nerve cell. Steep gradients of both Na+ and K+ are maintained across the plasma membranes of all cells via the Na—K pump.

TABLE 1

| ION | [INSIDE] (mM) | [OUTSIDE] (mM) |
|---|---|---|
| K+ | 140 | 5 |
| Na+ | 10 | 145 |

Such gradients provide the energy required for both the resting potential and the action potential of neurons. Concentration gradients for Na+ and K+ (in the axon of a mammalian neuron) are shown in Table 1. In a resting neuron, K+ is near electrochemical equilibrium, while a large electrochemical gradient exists for Na+. However, little trans-membrane movement of Na+ occurs because of the relative impermeability of the membrane in the resting state. In the resting state, the voltage-sensitive Na+ specific channels and the voltage-sensitive K+ specific channels are both closed. The passage of a nerve impulse along the axonal membrane is because of a transient change in the permeability of the membrane, first to Na+ and then to K+, which results in a predictable pattern of electrical changes propagated along the membrane in the form of the action potential.

The action potential of a neuron represents a transient depolarization and repolarization of its membrane. As alluded to above, the action potential is initiated by a stimulus, either from a sensory cell (e.g., hair cell of the cochlea) or an electrical impulse (e.g., an electrode of a cochlear implant). Specifically, upon stimulation the membrane becomes locally depolarized because of a rapid influx of Na+ through the voltage-sensitive Na+ channels. Current resulting from Na+ influx triggers depolarization in an adjacent region of the membrane, whereby depolarization is propagated along the axon. Following depolarization, the voltage-sensitive K+ channels open. Hyperpolarization results because of a rapid efflux of K+ ions, after which the membrane returns to its resting state. (See, for example, W. M. Becker & D. W. Deamer, *The World of the Cell,* 2nd Ed., pp. 616–640, Benjamin/Cummings, 1991. (hereafter Becker)) The above sequence of events requires only a few milliseconds.

Figure 3A:
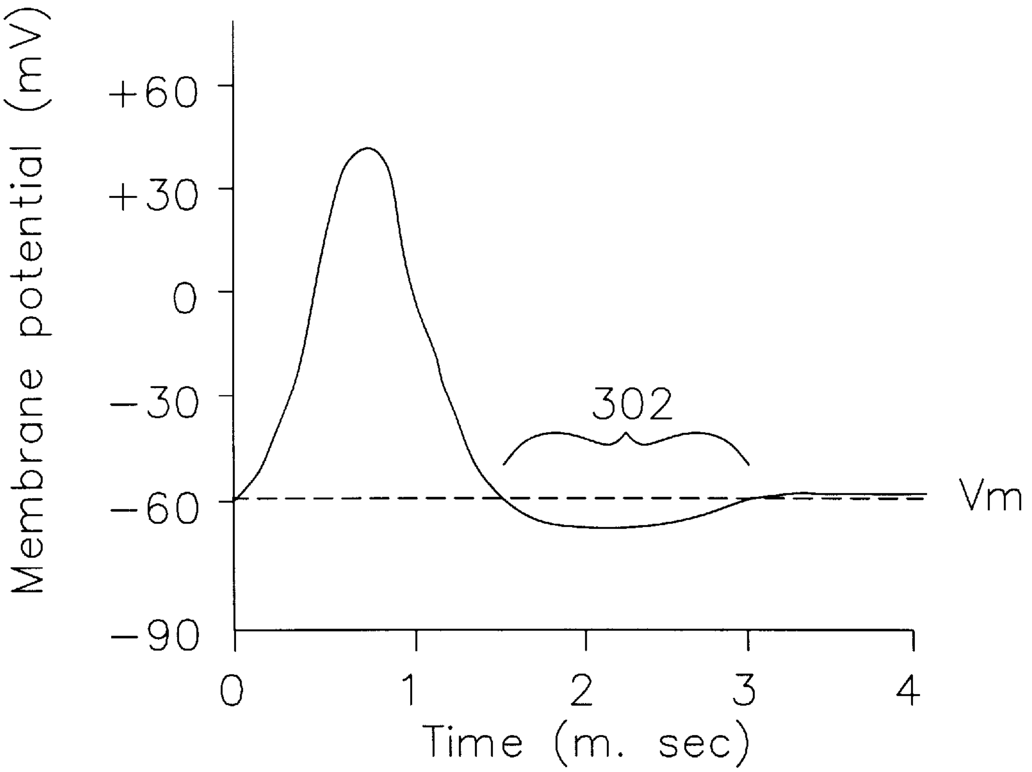
FIG. 3A is a diagram showing neuronal membrane potential during transmission of a nerve impulse.
Figure 3B:
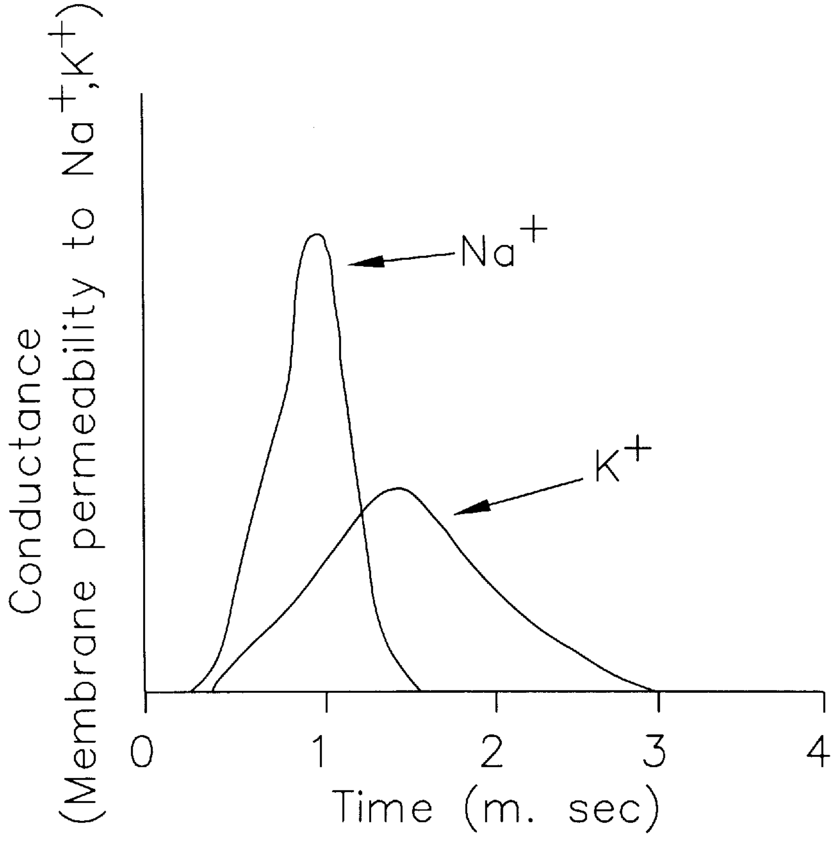
FIG. 3B is a diagram showing changes in permeability of the plasma membrane to Na+ and K+ during the generation of an action potential.

FIG. 3A shows a membrane potential of a nerve cell during elicitation of an action potential in response to a stimulus. During generation of an action potential, the membrane first becomes depolarized above a threshold level of at least 20 mV such that the membrane is rendered transiently very permeable to Na+, as shown in FIG. 3B, leading to a rapid influx of Na+. As a result, the interior of the membrane becomes positive for an instant and the membrane potential increases rapidly to about +40 mV. This increased membrane potential causes an increase in the permeability of the membrane to K+. A rapid efflux of K+ results and a negative membrane potential is reestablished at a level below the resting potential (Vm). In other words, the membrane becomes hyperpolarized 302 as shown in FIG. 3A. During this period of hyperpolarization 302, the sodium channels are inactivated and unable to respond to a depolarization stimulus. The period 302 during which the sodium channels, and therefore the axon, are unable to respond is called the absolute refractory period. The absolute refractory period ends when the membrane potential returns to the resting potential. At resting potential, the nerve cell can again respond to a depolarizing stimulus by the generation of an action potential. The period for the entire response of a nerve cell to a depolarizing stimulus, including the generation of an action potential and the absolute refractory period, is about 2.5 to about 4 ms. (See, for example, Becker, pp. 614–640)

As alluded to herein above, in a normal cochlea the inner hair cell-spiral ganglion is inherently "noisy" (i.e., there is a high background of activity in the absence of sound) resulting in spontaneous activity in the auditory nerve. Further, sound produces a slowly progressive response within and across fiber synchronization as sound intensity is increased. The absence of spontaneous activity in the auditory nerve can lead to tinnitus as well as other hearing-related problems.

According to the preferred embodiments of the present invention, the artificial induction of a random pattern of activation in the auditory nerve of a tinnitus patient or a hard-of-hearing patient mimics the spontaneous neural activation of the auditory nerve, which routinely occurs in an individual with normal hearing and lacking tinnitus. The artificially induced random pattern of activation of the auditory nerve is hereafter called "pseudospontaneous". In the case of an individual having a damaged cochlea, such induced pseudospontaneous stimulation activation of the auditory nerve may be achieved, for example, by the delivery of a high rate pulse train directly to the auditory nerve via a cochlea implant. Alternatively, in the case of a patient with a functional cochlea, pseudospontaneous stimulation of the auditory nerve may be induced directly by stimulation via an appropriate middle ear implantable device. Applicant has determined that by inducing pseudospontaneous activity and desynchronizing the auditory nerve, the symptoms of tinnitus may be alleviated.

Figure 11:
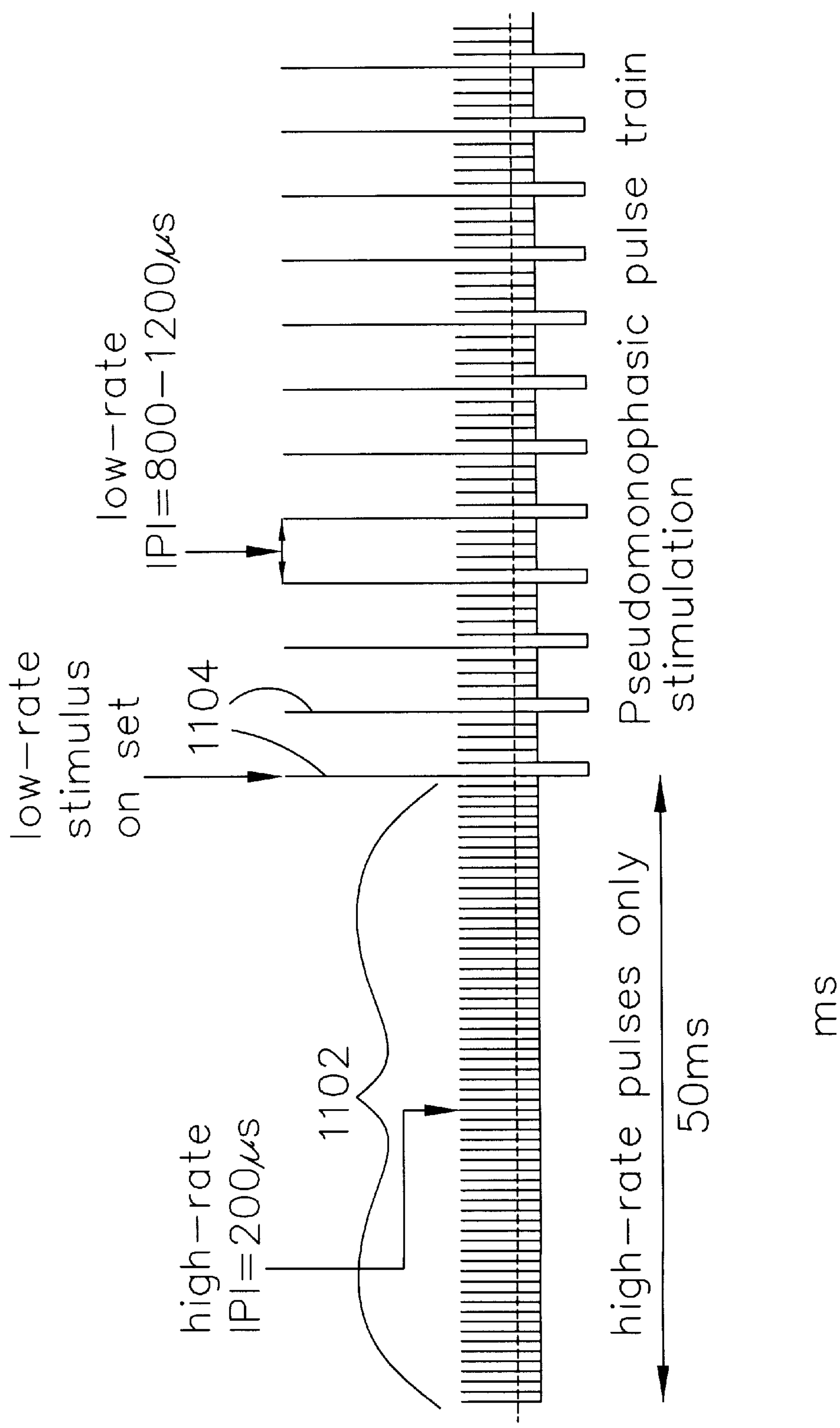
FIG. 11 is a diagram showing a preferred embodiment of a driving signal for an auditory nerve according to the present invention.

Preferred embodiments of the present invention emphasize stochastic independence across an excited neural population. A first preferred embodiment of a neural driving signal according to the present invention that generates pseudospontaneous neural activity will now be described. In particular, high rate pulse trains according to the first preferred embodiment can produce random spike patterns in auditory nerve fibers that are statistically similar to those produced by spontaneous activity in the normal spiral ganglion cells. Simulations of a population of auditory nerve fibers illustrate that varying rates of pseudospontaneous activity can be created by varying the intensity of a fixed amplitude, high rate pulse train stimulus. Further, electrically-evoked compound action potentials (EAPs) recorded in a human cochlear implant subject verify that such a stimulus can desynchronize the nerve fiber population. Accordingly, the preferred embodiments according to the present invention can eliminate a major difference between acoustic and electric hearing. An exemplary high rate pulse train driving signal 1102 according to the first embodiment is shown in FIG. 11.

A population of 300 modelled auditory nerve fibers (ANF) has been simulated on a Cray C90 (vector processor) and IBM SP-2 (parallmodel used a stochastic he ANF model used a stochastic representation of each node of Ranvier and a deterministic representation of the internode. Recordings were simulated at the 13th node of Ranvier, which approximately corresponds to the location of the porus of the internal auditory canal assuming the peripheral process has degenerated. Post-stimulus time (PST) histograms and interval histograms were constructed using 10 ms binning of the peak of the action potential. As is well-known in the art, a magnitude of the EAPs is measured by the absolute difference in a negative peak (N1) after pulse onsets and a positive peak (P2) after pulse onsets.

Stimuli presented to the ANF model were a high rate pulse train of 50 $\mu$s monophasic pulses presented at 5 kHz for 18 ms from a point source monopolar electrode located 500 $\mu$m perpendicularly from the peripheral terminals of the axon population. All acoustic nerve fibers were simulated as being in the same geometric location. Thus, each simulation can be considered to represent either 300 fibers undergoing one stimulus presentation or a single fiber undergoing 300 stimulus presentations. In addition, a first stimulus of the pulse train was of sufficient magnitude to evoke a highly synchronous spike in all 300 axons; all subsequent pulses are of an equal, smaller intensity. The first stimulus substantially increased computational efficiency by rendering all fibers refractory with the first pulse of the pulse train.

Two fibers were simulated for eight seconds using the parameters described above. Spike times were determined with one As precision and assembled into 0.5 ms bins. Conditional mean histograms, hazard functions and forward recurrence time histograms were calculated (using 0.5 ms bins because of the small number of spikes (1000) simulated) as known to one of ordinary skill in the art. For example, see *Analysis of Discharges Recorded Simultaneously From Pairs of Auditory Nerve Fibers*, D. H. Johnson and N. Y. S. Kiang, Journal of Biophysics, 16, 1976, pages 719–734, (hereafter Johnson and Kiang), hereby incorporated by reference. See also "*Pseudospontaneous Activity: Stochastic Independence of Auditory Nerve Fibers with Electrical Stimulation*," J. T. Rubinstein, et al., pages 1–18, 1998, hereby incorporated by reference.

Figure 4A:
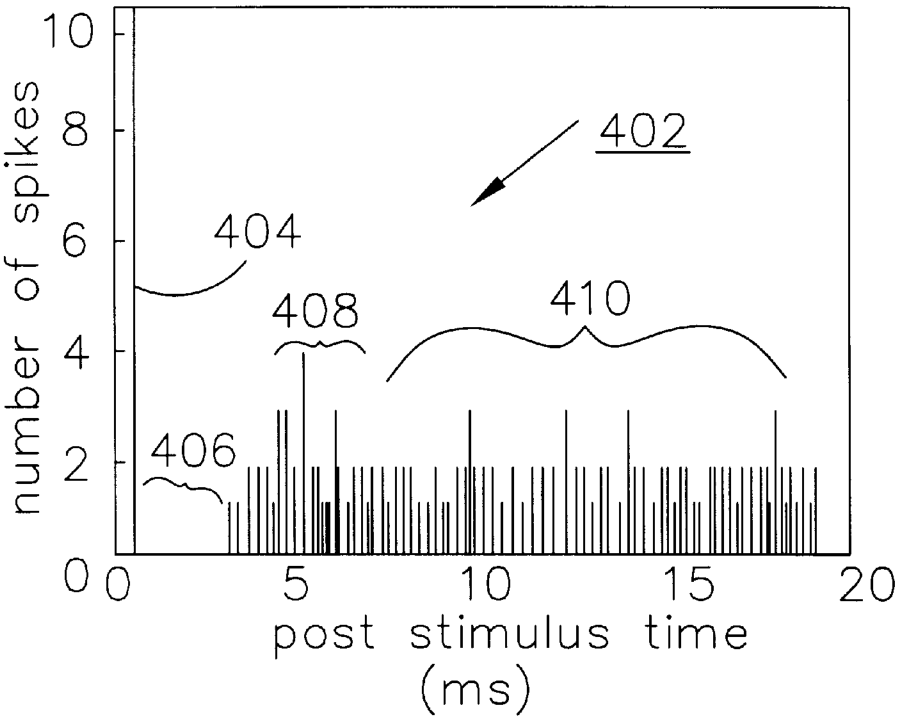
FIGS. 4A and 4B are diagrams showing histograms of modeled responses of the human auditory nerve to a high rate pulse train.

FIG. 4A shows a post-stimulus time (PST) histogram 402 of discharge times from the ANF model with a stimulus amplitude of 325, $\mu$A. A highly synchronous response 404 to a first, higher amplitude pulse was followed by a "dead time" 406. Then, an increased probability of firing 408 was followed by a fairly uniform firing probability 410. The y-axis of the PST histogram has been scaled to demonstrate temporal details following the highly synchronous response to the first pulse. There was a small degree of synchronization with the stimulus as measured by a vector strength of 0.26.

Figure 4B:
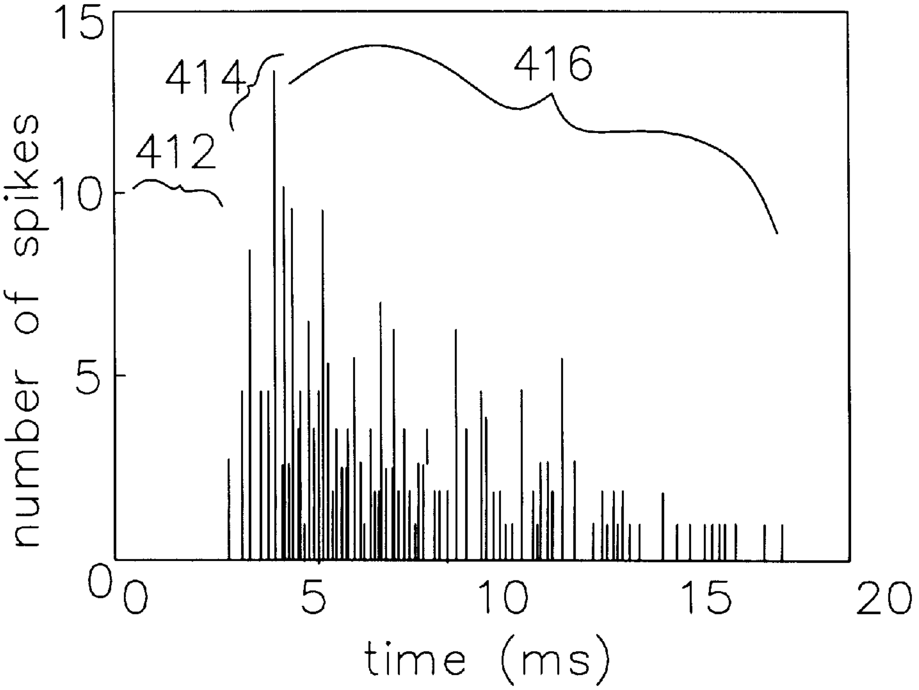
Figure 5A:
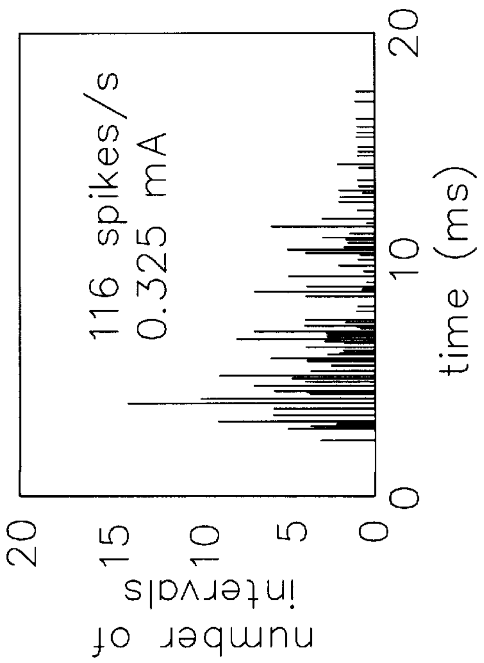
FIGS. 5A–5D are diagrams showing interval histograms of modeled responses of the human auditory nerve to a high rate pulse train at various intensities.
Figure 5B:
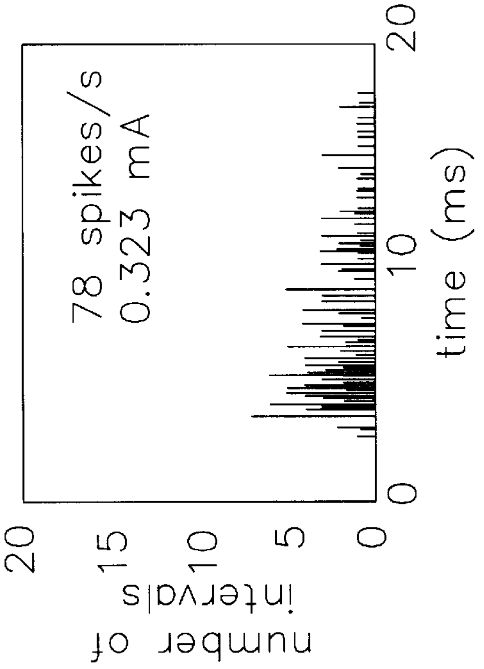
Figure 5C:
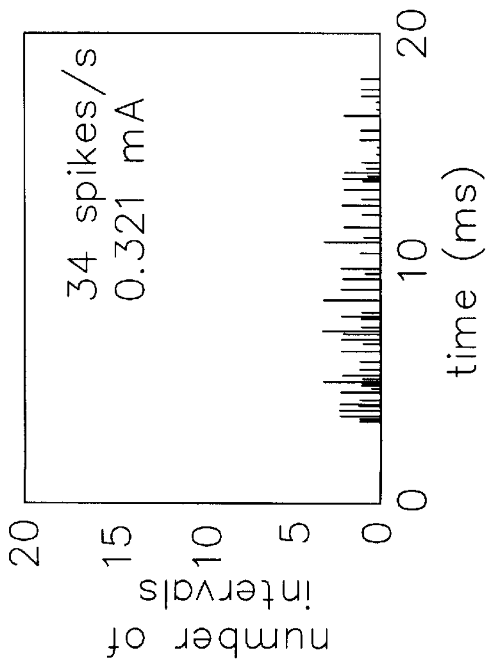
Figure 5D:
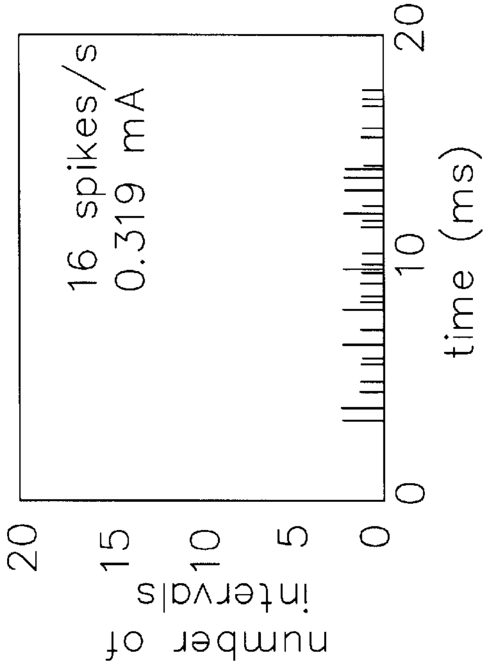

FIG. 4B shows an interval histogram of the same spike train. As shown in FIG. 4B, a dead time 412 was followed by a rapid increase in probability 414 and then an exponential decay 416. The interval histogram is consistent with a Poisson process following a dead time, a renewal process, and greatly resembles interval histograms of spontaneous activity in the intact auditory nerve. These simulation results corresponds to a spontaneous rate of 116 spikes/second measured during the uniform response period of 7 to 17 ms.

As shown in FIGS. 5A–5D, when the stimulus intensity was varied in the ANF model, the firing rate and shape of the PST and interval histograms changed. FIGS. 5A–5D show four interval histograms of a response to a 5 kHz pulse train at different stimulus intensities that demonstrated a range of possible firing rates. The histograms changed shape with changes in pseudospontaneous rate in a manner consistent with normal auditory nerve fibers. All demonstrate Poisson-type intervals following a dead-time. The firing rate during the period of uniform response probability is given in the upper right corner of each plot. Similarly, as respectively shown in FIGS. 8 and 9, a conditional mean histogram and a hazard function for a single "unit" simulated for eight seconds were within standard deviations of theoretical limits. Thus, the conditional mean histogram was "constant," which is consistent with a renewal process, and indicated that a firing probability was not affected by intervals prior to the previous spike. The hazard function was also "constant" after a dead-time, followed by a rapidly rising function. Thus, both plots were consistent with a renewal process much like spontaneous activity, at least for the intervals for which the ANF model had an adequate sample.

Figure 6:
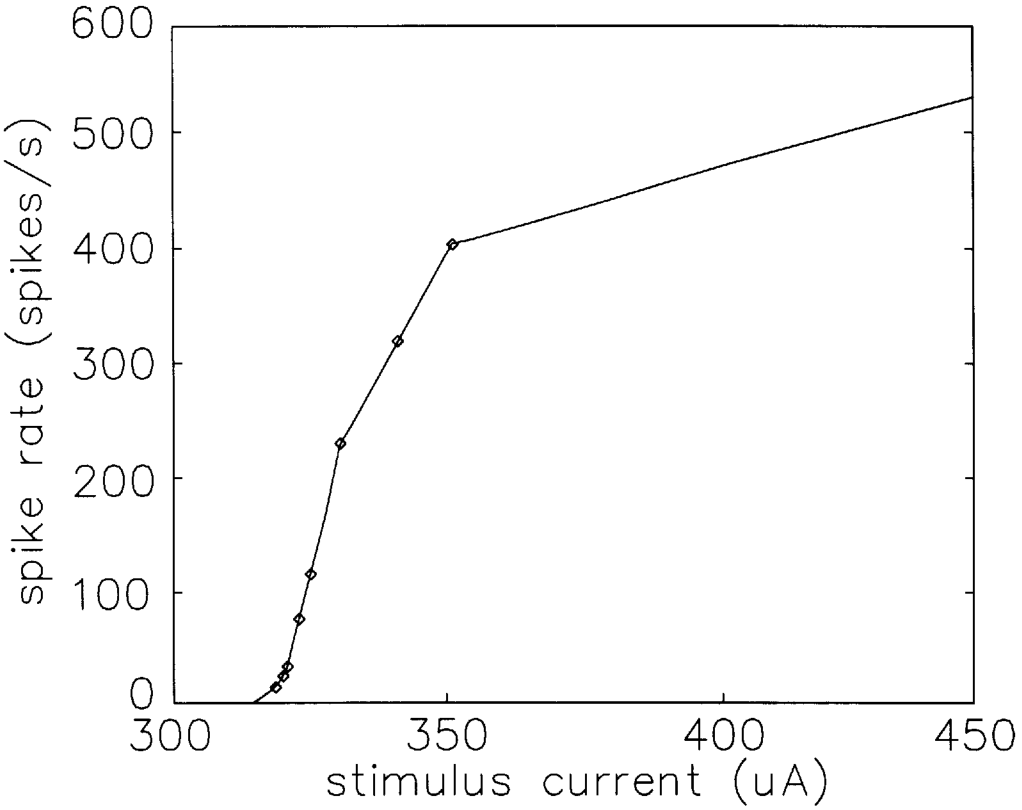
FIG. 6 is a diagram showing a relationship between stimulus intensity and spike rate.

FIG. 6 shows the relationship between stimulus intensity and pseudospontaneous rate. A full range of spontaneous rates, previously known in animal (from zero to approximately 150 spikes/s), was demonstrated over a relatively narrow range of stimulus intensity for the high rate pulse train stimulation in a computer simulation. Since there is minimal synchronization with the stimulus, compound action potentials in response to individual pulses would be expected to be small or unmeasurable.

Figure 7:
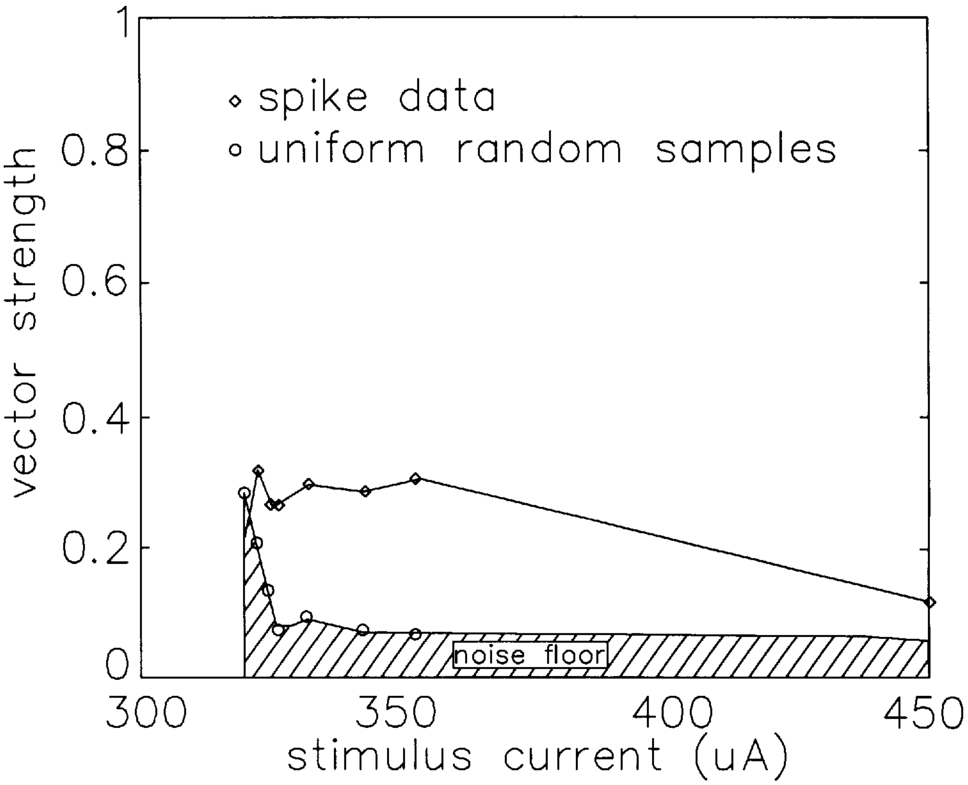
FIG. 7 is a diagram showing a relationship between stimulus intensity and vector strength.

Normal spontaneous activity is independent across neurons. Since pseudospontaneous activity is driven by a common stimulus, one measure of the relative degree of dependence/independence of individual nerve fibers within the auditory nerve was vector strength. Vector strength is a measure of the degree of periodicity or synchrony with the stimulus. Vector strength is calculated from period histograms and varies between 0 (no periodicity) and 1 (perfect periodicity). If vector strength is "high" then each fiber will be tightly correlated with the stimulus and two such fibers will be statistically dependent. If vector strength is "low" then two such fibers should be independent. As shown in FIG. 7, a relationship between stimulus intensity and vector strength is nonzero, but is below or near a noise floor at all intensities tested for the high rate pulse train stimulation. In addition, there is little effect of stimulus amplitude on synchrony. A noise floor for the vector strength calculation was obtained from 500 samples of a set of uniform random numbers whose size is equal to the number of spikes recorded at that stimulus intensity.

Figure 8A:
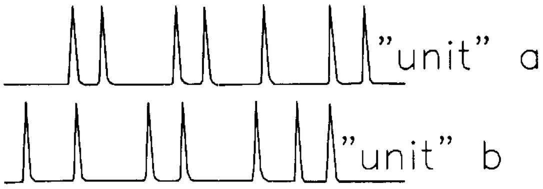
FIG. 8A is a diagram showing two exemplary unit waveforms.
Figure 8B:
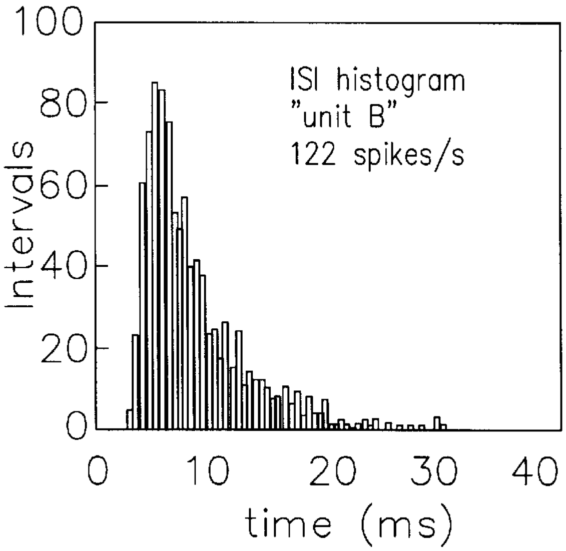
FIG. 8B is a diagram showing an interval histogram.
Figure 8C:
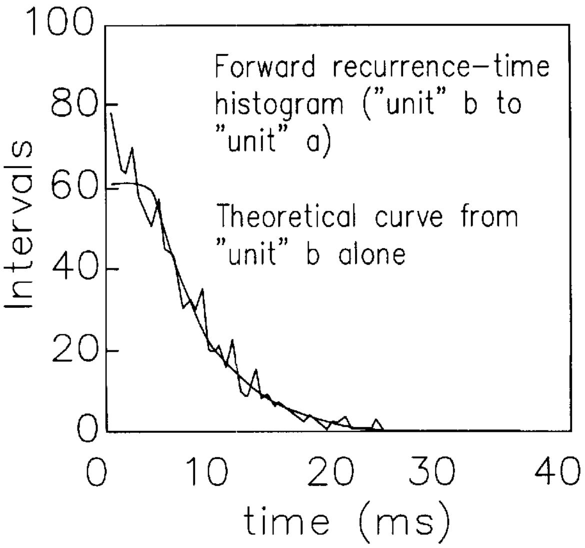
FIGS. 8C–8D are diagrams showing exemplary recurrence time data.
Figure 8D:
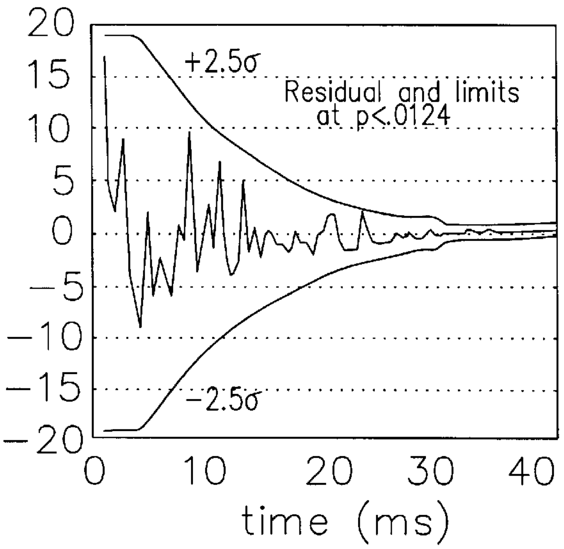
Figure 9:
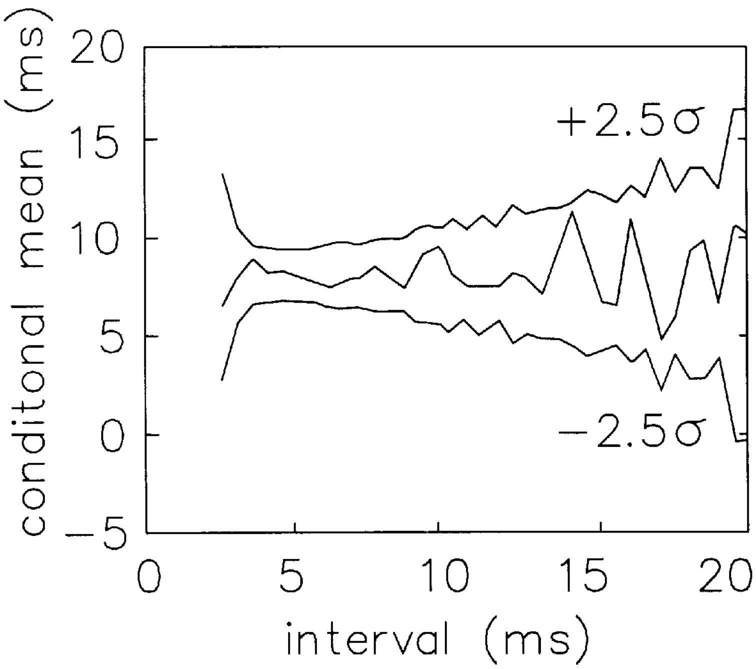
FIG. 9 is a diagram showing an exemplary conditional mean histogram.
Figure 10:
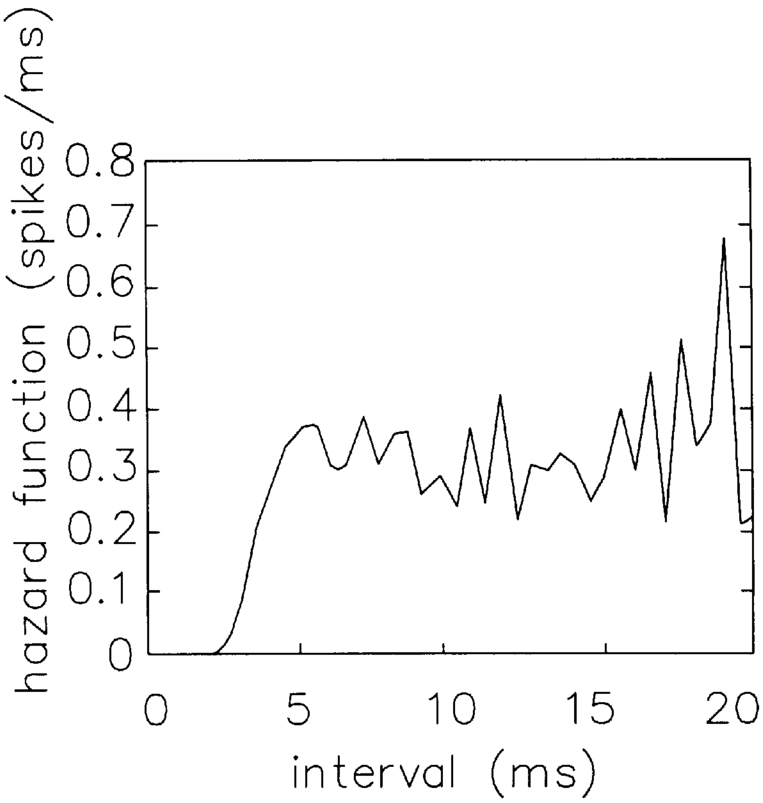
FIG. 10 is a diagram showing an exemplary unit hazard function.

A more rigorous evaluation of fiber independence is a recurrence-time test. (See, for example, Johnson and Kiang.) By using a bin size of 0.5 ms, useful recurrence-time histograms were assembled from two 2-second spike trains of the ANF model simulation. FIG. 8A shows a 50 ms sample of spike activity from two "units" (i.e., two simulated neurons). FIG. 8B shows an ISI histogram from an eight second run of "unit" b. FIG. 8C shows a forward recurrence-time histogram of "unit" b to "unit" a, and a theoretical recurrence-time from "unit" b assuming that "units" a and b are independent. The theoretical forward recurrence-time curve is flat during the refractory period. Theoretical limits are shown at $\rho<0.0124$ (2.5 standard deviations). FIG. 8D shows residuals calculated by subtracting the curves in FIG. 8C. Thus, the ANF model demonstrated pseudospontaneous activity caused by high rate pulse train stimulation.

As described above, driving a population of simulated auditory nerve fibers with high rate pulses according to the first preferred embodiment produces independent spike trains in each simulated fiber after about 20 ms. FIG. 11 shows an exemplary pseudospontaneous driving signal having high rate pulse train driving signal 1102 as a conditioner and a stimulus 1104. This pseudospontaneous activity is consistent with a renewal process and yields statistical data comparable to true spontaneous activity within computational limitations.

However, the present invention is not intended to be limited to this. For example, broadband additive noise (e.g., because of rapid signal amplitude transitions) can evoke pseudospontaneous activity similar to the high rate pulse train. Any signal that results in pseudospontaneous activity that meets the same tests of independence as true spontaneous activity can be used as the driving signal.

Figure 12:
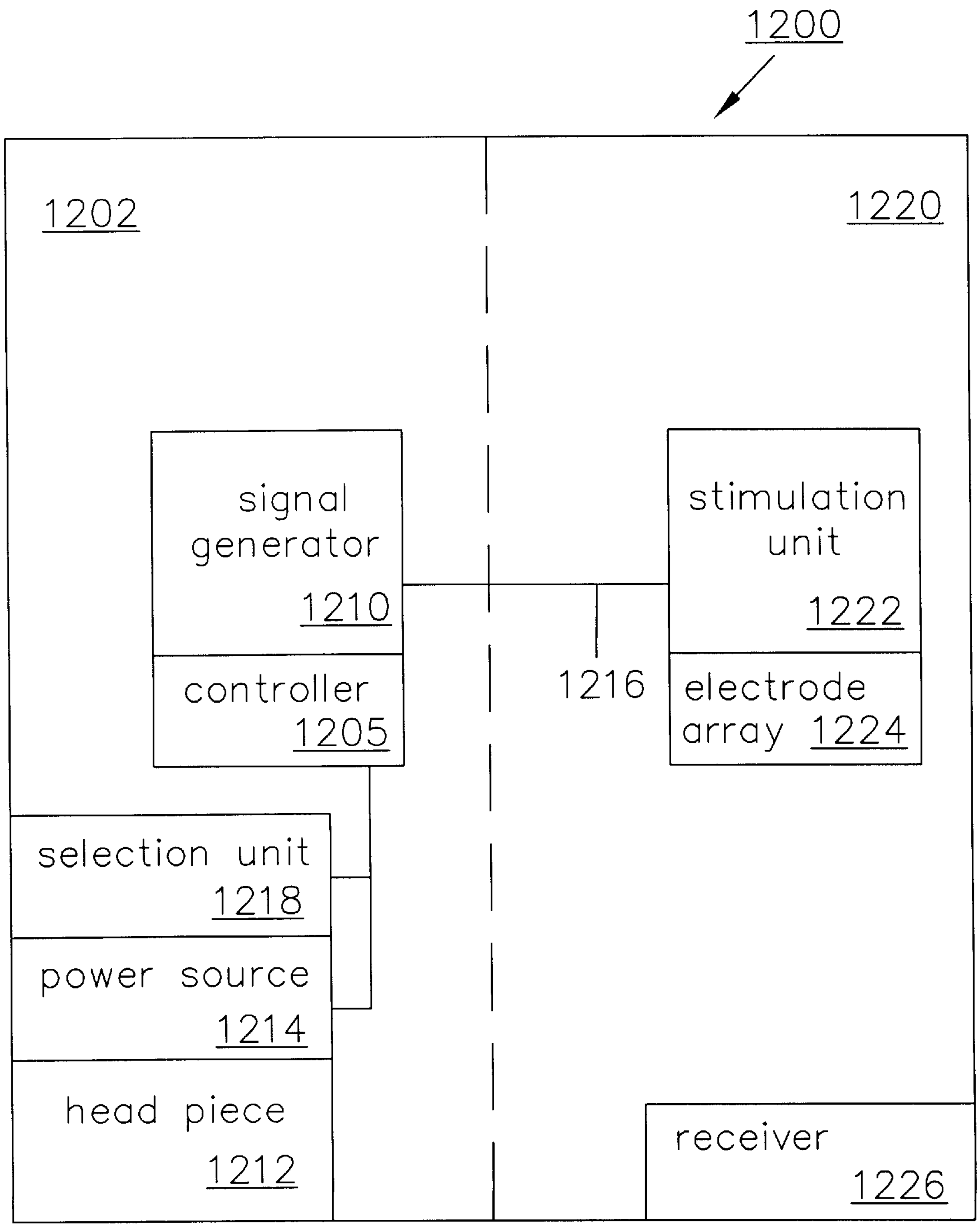
FIG. 12 is a diagram showing a preferred embodiment of an apparatus that provides a driving signal to the auditory nerve according to the present invention.

A second preferred embodiment of an apparatus to generate and apply a pseudospontaneous driving signal to an auditory nerve according to the present invention will now be described. As shown in FIG. 12, the second preferred embodiment includes an inner ear stimulation system 1200 that directly electrically stimulates the auditory nerve (not shown). The inner ear stimulation system 1200 can include two components: (1) a wearable or external system, and (2) an implantable system. An external system 1202 includes a signal generator 1210. The signal generator 1210 can include a battery, or an additional equivalent power source 1214, and further includes electronic circuitry, typically including a controller 1205 that controls the signal generator 1210 to produce prescribed electrical signals.

The signal generator 1210 produces a driving signal or conditioner 1216 to generate pseudospontaneous activity in the auditory nerve. For example, the signal generator can produce a driving signal in accordance with the first preferred embodiment. The signal generator 1210 can be any device or circuit that produces a waveform that generates pseudospontaneous activity. That is the signal generator 1210 can be any device that produce a pseudospontaneous driving signal. For example, an application program operating on a special purpose computer or microcomputer combined with an A/D converter, and LC resinating circuit, firmware or the like can be used, depending on the exact form of the pseudospontaneous driving signal. Further, the inner ear stimulation system 1200 can suppress or effectively alleviate perhaps or eliminate tinnitus in a patient. The signal generator 1210 can vary parameters such as the frequency, amplitude, pulse width of the driving signal 1216. The external system 1202 can be coupled to a head piece 1212. For example, the head piece can be an ear piece worn like a hearing aid. Alternatively, the external system 1202 can be a separate unit.

As shown in FIG. 12, the controller 1205 is preferably implemented on a microprocessor. However, the controller 1205 can also be implemented on a special purpose computer, microcontroller and peripheral integrated circuit elements, an ASIC or other integrated circuit, a hardwired electronic or logic circuit such as a discrete element circuit, a programmable logic device such as a PLD, PLA, FGPA or PAL, or the like. In general, any device on which a finite state machine capable of controlling a signal generator and implementing the flowchart shown in FIG. 13 can be used to implement the controller 1205.

As shown in FIG. 12, an implantable system 1220 of the inner ear stimulation system 1200 can include a stimulator unit 1222 directly coupled to the auditory nerve. For example, the stimulator unit 1222 can include an electrode array 1224 or the like for implantation into the cochlea of a patient. The electrode array 1224 can be a single electrode or multiple electrodes that stimulate several different sites at arranged sites along the cochlea to evoke nerve activity normally originating from the respective sites. The stimulation unit 1222 is preferably electrically coupled to the auditory nerve. The stimulation unit 1222 can be located in the inner ear, middle ear, ear drum or any location that effectively couples the stimulation unit 1222 to the auditory nerve directly or indirectly, and produces pseudospontaneous activity in the auditory nerve caused by the stimulation unit 1222. In addition, the implantable system 1220 can be directly or indirectly coupled to the external system 1202.

If indirectly coupled to the external system 1202, the stimulator 1222 can include a receiver 1226. The receiver 1226 can receive information and power from corresponding elements in the external system 1202 through a tuned receiving coil (not shown) attached to the receiver 1226. The power, and data as to which electrode to stimulate, and with what intensity, can be transmitted across the skin using an inductive link from the external signal generator 1210. For example, the receiver 1226 can then provide electrical stimulating pulses to the electrode array 1224. Alternatively, the stimulation unit 1222 can be directly coupled to the external system 1202 via a conductive medium or the like.

The patient's response to electrical stimulation by the driving signal 1216 can be subsequently monitored or tested. The results of these tests could be used to modify the driving signal 1216 or to select from a plurality of driving signals using a selection unit 1218.

When the stimulation unit 1222 includes the electrode array 1224, the stimulator unit 1222 can operate in multiple modes such as, the "multipolar" or "common ground" stimulation, and "bipolar" stimulation modes. However, the present invention is not intended to be limited to this. For example, a multipolar or distributed ground system could be used where not all other electrodes act as a distributed ground, and any electrode could be selected at any time to be a current source, current sink, or to be inactive during either stimulation phase with suitable modification of the receiver-stimulator. Thus, there is great flexibility in choice of stimulation strategy to provide the driving signal 1216 to the auditory nerve. However, the specific method used to apply the driving signal must result in the pseudospontaneous activity being generated. In addition, the present invention is not intended to be limited to a specific design of the electrode array 1224, and a number of alternative electrode designs as have been described in the prior art could be used.

Figure 13:
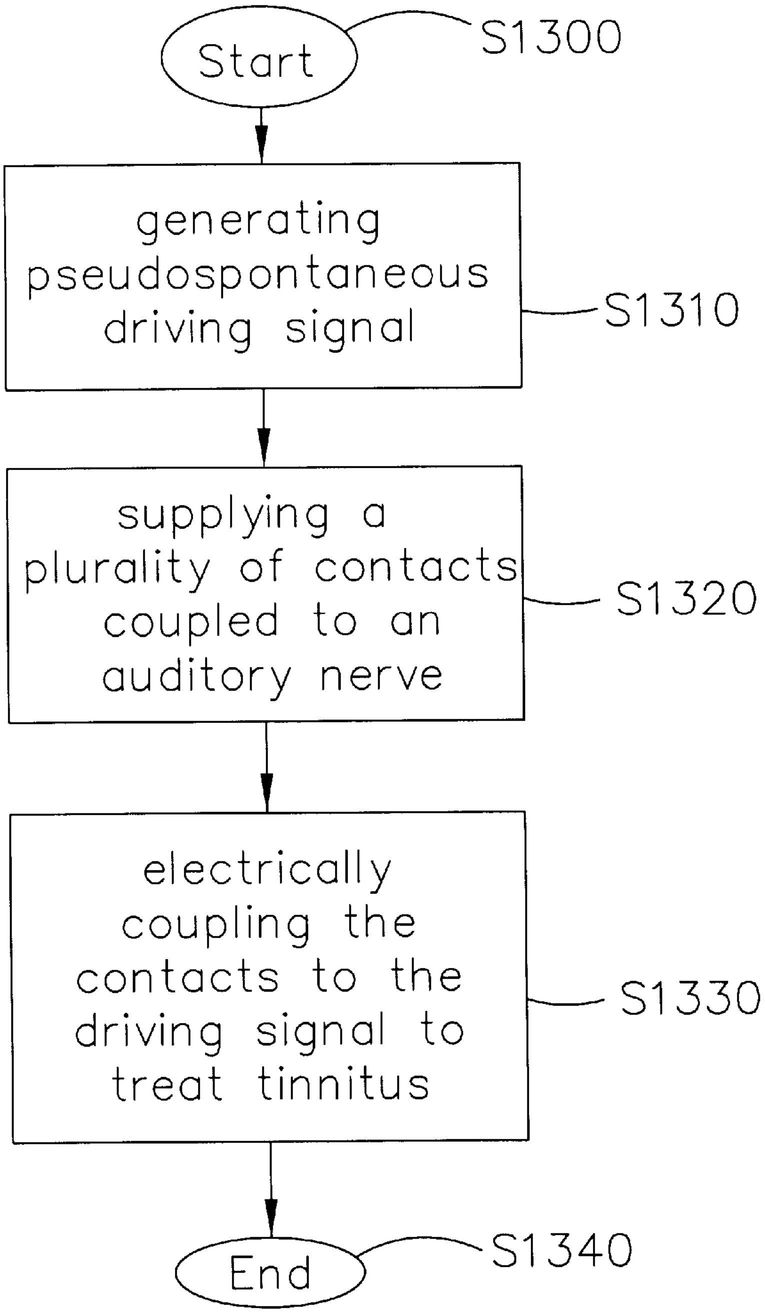
FIG. 13 is a diagram showing a flowchart showing a preferred embodiment of a method for suppressing tinnitus.
Figure 14:
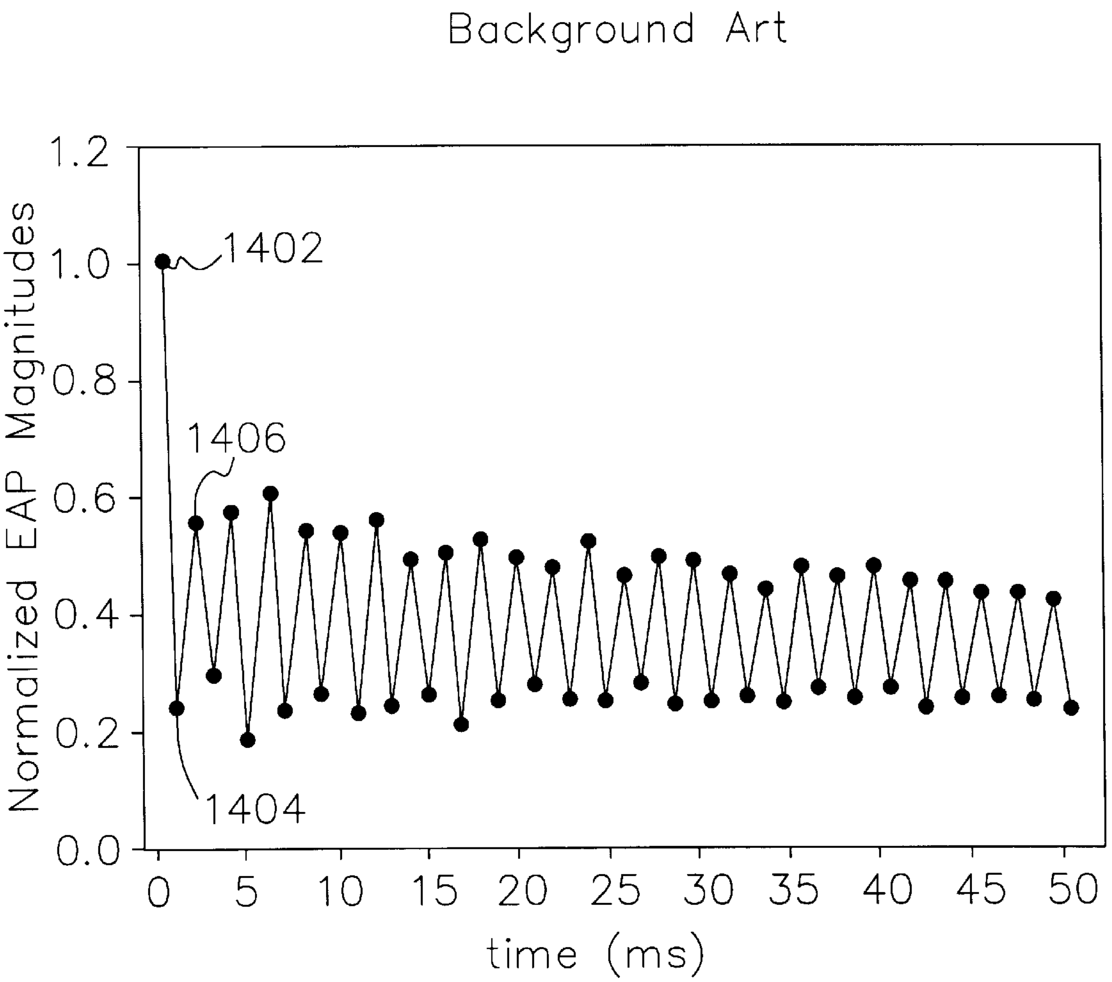
FIG. 14 is a diagram showing related art EAP N1P1 magnitudes in a human subject subjected to a low rate stimulus.

A third preferred embodiment of a the invention comprises a method for treating tinnitus. A preferred method for treating tinnitus according to the present invention will now be described. As shown in FIG. 13, the process starts in step S1300. From step S1300, control continues to step S1310. In step S1310, a pseudospontaneous driving signal is generated. For example, a driving signal according to the first preferred embodiment can be generated or selected via a selection unit as described in the second preferred embodiment in step S1310. An exemplary stimulus paradigm for a high-rate pulse train stimulation 1102 is shown in FIG. 11. As shown in FIG. 11, the high rate pulses 1102 had a constant amplitude, pulse width and frequency of approximately 5 kHz. From step S1310, control continues to step S1320.

In step S1320, a plurality of contacts or electrodes are preferably supplied to an auditory nerve or the like in the ear. The plurality of contacts can have a prescribed arrangement such as a tonotopic arrangement. Alternatively, a single electrode can be provided to the cochlea using a middle ear implant electrically coupled to the auditory nerve and cochlea in the inner ear or the like. Given the broader range of electrical thresholds in the auditory nerve (approximately 12 dB), with multiple electrodes it may be possible to maintain near physiologic rates across most of the auditory nerve but regions of below and above normal activity can occur. From step S1320, control continues to step S1330.

In step S1330, the driving signal is electrically coupled to the plurality of contacts to suppress tinnitus. From step S1330, control continues to step S1340 where the process is completed. The method according to the third preferred embodiment can optionally include a feed-back test loop to modify or merely select one of a plurality of selectable pseudospontaneous driving signals based on a subset of parameters specifically designed and evaluated for an individual patient.

As described above, the preferred embodiments according to the present invention have various advantages. The preferred embodiments generate stochastically independent or pseudospontaneous neural activity, for example, in an auditory nerve to suppress tinnitus and a stimulus which evokes pseudospontaneous activity should not be perceptible over the long term as long as the rate is physiologic. Thus, a major difference between acoustic and electric hearing can be superceded. Further, an inner ear or middle ear auditory prosthesis can be provided that suppresses tinnitus. In addition, the preferred embodiments provide an apparatus and method that delivers a prescribed signal such as a high rate pulse train to generate neural pseudospontaneous activity and may be used in conjunction with a suitable auditory prosthesis to increase hearing capability by providing a prescribed signal to auditory neurons.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method for generating pseudospontaneous activity in an auditory nerve, comprising:

generating a pseudospontaneous driving electrical signal; and applying the pseudospontaneous driving electrical signal to the auditory nerve to generate pseudospontaneous activity in the auditory nerve.

2. The method of claim 1, wherein the pseudospontaneous driving electrical signal includes a high rate pulse train, and wherein the applying step generates substantially continuous pseudospontaneous activity.

3. The method of claim 1, wherein the pseudospontaneous driving electrical signal includes a broadband noise.

4. The method of claim 1, wherein the pseudospontaneous driving electrical signal includes at least fluctuations in amplitude greater than a prescribed amount at a frequency above approximately 2 kHz.

5. The method of claim 1, wherein the applying step comprises applying current to the auditory nerve, wherein the auditory nerve comprises a plurality of nerve fibers, and wherein the pseudospontaneous activity is demonstrated by statistically independent activity in the plurality of nerve fibers.

6. The method of claim 1, wherein the applying step further comprises effectively suppressing tinnitus in a patient.

7. The method of claim 1, wherein the applying step is performed by one of a middle ear implant and an inner ear implant, and wherein the generating step is performed by a signal generator.

8. The method of claim 1, wherein the auditory nerve comprises a plurality of nerve fibers, and wherein the pseudospontaneous driving electrical signal comprises one or more signals that generate a substantially maximum firing rate of the plurality of neurons.

9. A neural prosthetic apparatus for treatment of a patient with tinnitus, comprising:

a stimulation device that outputs one or more electrical signals that include transitions between first and second amplitudes occurring at a frequency greater than approximately 2 kHz;

an arrangement of at least one electrical contact adapted to be affixed within the cochlea of the patient; and electrical coupling means for electrically coupling the at least one electrical contact to the stimulation device, and wherein the neural prosthetic apparatus effectively alleviates the tinnitus of the patient.

10. The apparatus according to claim 9, wherein the electrical signals include a high rate pulse train.

11. The apparatus according to claim 9, wherein the electrical signals cause pseudospontaneous activity in an auditory nerve.

12. The apparatus according to claim 9, wherein the neural prosthetics apparatus is at least one of an inner ear implant and a middle ear implant.

13. The apparatus according to claim 9, wherein the first and second amplitudes are positive and negative, respectively, and wherein the first and second amplitudes are equal in magnitude.

14. A method for treating a patient with tinnitus, comprising:

outputting one or more pseudospontaneous driving signals; and delivering the one or more pseudospontaneous driving signals to an auditory nerve, wherein the one or more pseudospontaneous driving signals generate pseudospontaneous activity to effectively alleviate the tinnitus of the patient.

15. The method according to claim 14, wherein the one or more pseudospontaneous driving signals includes a high rate pulse train having a frequency above 2 kHz.

16. A neural prosthetic apparatus for treatment of a patient with tinnitus, comprising:

a pseudospontaneous signal generator that generates an electrical signal;

an arrangement of at least one electrical contact adapted to be affixed in the middle ear of the patient; and a stimulation device coupled to the generator that applies the electrical signal to the at least one electrical contact, the electrical signal capable of generating pseudospontaneous activity in the auditory nerve, and wherein the neural prosthetic apparatus effectively alleviates the tinnitus of the patient.

17. The apparatus of claim 16, wherein the electrical signal transitions between first and second amplitudes at a frequency above 2 kHz.

18. The apparatus of claim 16, wherein the electrical contact is adapted to be affixed nearby a round window of the patient.

19. The apparatus of claim 18, wherein the electrical contact is adapted to be electrically coupled to the auditory nerve.

20. The apparatus of claim 16, wherein the electrical contact is adapted to be affixed nearby the cochlea of the patient.

21. An apparatus that generates pseudospontaneous activity in at least one auditory nerve, comprising:

a device that generates a pseudospontaneous driving signal; and a stimulation device coupled to the device, the stimulation device capable of delivering the pseudospontaneous driving signal to the at least one auditory nerve, wherein the pseudospontaneous driving signal induces pseudospontaneous activity in the at least one auditory nerve.

22. The apparatus of claim 21, wherein the device is one of a circuit, a resonating circuit and a signal generator.

23. The apparatus of claim 21, wherein the pseudospontaneous driving signal includes at least fluctuations in amplitude greater than a prescribed amount at a frequency above approximately 2 kHz.

* * * * *